(12) United States Patent
Arimoto et al.

(10) Patent No.: US 8,699,031 B2
(45) Date of Patent: Apr. 15, 2014

(54) OPTICAL MEASUREMENT DEVICE

(75) Inventors: Kimihiko Arimoto, Kyoto (JP); So Takagi, Kyoto (JP)

(73) Assignee: Horiba, Ltd., Kyoto-shi (JP)

( * ) Notice: Subject to any disclaimer, the term of this patent is extended or adjusted under 35 U.S.C. 154(b) by 312 days.

(21) Appl. No.: 13/170,057

(22) Filed: Jun. 27, 2011

(65) Prior Publication Data

US 2011/0317166 A1 Dec. 29, 2011

(30) Foreign Application Priority Data

Jun. 28, 2010 (JP) ................................. 2010-146089
May 17, 2011 (JP) ................................. 2011-110692

(51) Int. Cl.
*G01N 21/00* (2006.01)
*G01N 21/03* (2006.01)

(52) U.S. Cl.
CPC .................. *G01N 21/0303* (2013.01)
USPC .......................................................... 356/440

(58) Field of Classification Search
None
See application file for complete search history.

(56) References Cited

U.S. PATENT DOCUMENTS

| | | | | |
|---|---|---|---|---|
| 4,834,534 A * | 5/1989 | Wiget | ............................ | 356/246 |
| 5,078,493 A * | 1/1992 | Evens et al. | .................... | 356/246 |
| 5,408,326 A * | 4/1995 | Wang | ............................ | 356/410 |
| 7,369,226 B1 * | 5/2008 | Hewitt | ........................... | 356/246 |
| 7,518,720 B2 * | 4/2009 | Kolp et al. | ..................... | 356/246 |
| 7,542,143 B2 * | 6/2009 | Simpson et al. | ............. | 356/246 |
| 7,961,310 B1 * | 6/2011 | Milosevic | ..................... | 356/246 |
| 2004/0080744 A1 * | 4/2004 | Hobbs | ........................... | 356/246 |
| 2005/0121615 A1 * | 6/2005 | Prater et al. | .................. | 250/343 |
| 2006/0180517 A1 * | 8/2006 | Frazier | .......................... | 209/579 |
| 2007/0064226 A1 * | 3/2007 | Kolp et al. | ..................... | 356/246 |
| 2010/0231910 A1 * | 9/2010 | Mavliev | ....................... | 356/246 |

FOREIGN PATENT DOCUMENTS

JP          2007-093598 A          4/2007

* cited by examiner

*Primary Examiner* — Gregory J Toatley
*Assistant Examiner* — Juan D Valentin, II
(74) *Attorney, Agent, or Firm* — Alleman Hall McCoy Russell & Tuttle LLP

(57) ABSTRACT

An optical measurement device is adapted to measure characteristics of a measurement targeted fluid based on a transmitted inspection light. The device comprises a cell having an internal space for accommodating the measurement targeted fluid to flow therein and having a pair of opposing through holes for transmitting the inspection light, each of the through holes sealed with a transparent member. The device includes a projection optical system member having a port for projecting the inspection light and a light-receiving optical system member having a port for receiving the inspection light transmitted through the internal space. A base member is provided for supporting the cell, the projection optical system member, and the light-receiving optical system member in a configuration with gaps between the cell and the respective optical system members to accommodate movement in a predetermined range along a direction perpendicular to an optical axis of the inspection light.

7 Claims, 10 Drawing Sheets

OPTICAL MEASUREMENT DEVICE

TECHNICAL FIELD

The present invention relates to an optical measurement device for measuring characteristics such as a degree of contamination or concentration of a fluid to be measured (referred to as "measurement targeted fluid" hereinafter) by transmitting an inspection light through the measurement targeted fluid such as a chemical solution for use in, e.g., a manufacturing process of a semiconductor and the like.

BACKGROUND ART

For example, in the case where a contamination of a fluid such as an engine oil is measured, there is known a method of measuring a degree of contamination based on a transmittance obtained by irradiating the fluid with an inspection light.

As a specific example, as disclosed in Patent Literature 1, there is a configuration such that, a projection optical system member provided with a projection port for projecting an inspection light and a light-receiving optical system member provided with an introduction port for receiving the inspection light are respectively attached to opposing surfaces of a cell so that the inspection light projected from the projection port passes through a fluid inside the cell via a window of the cell so as to be received by the introduction port.

By the way, for example, in such a case of measuring a degree of contamination of a cleaning chemical solution for cleaning a semiconductor wafer, it is necessary to use a corrosion-resistant material such as PTFE (Teflon) as a cell material.

However, since PTFE has a large rate of change in shape with respect to a temperature change, with an aspect of the projection optical system member and the light-receiving optical member attached to the cell as mentioned above, in the case where chemical solutions at various temperatures are used as in the case of, e.g., a sheet-type semiconductor manufacturing apparatus, etc., the cell is deformed due to differences in temperature of every chemical solution so as to cause such as a shift between an optical axis of the projection optical system member and that of the light-receiving system member, and therefore the measurement accuracy cannot be ensured.

Citation List
Patent Literature
Patent Literature 1: JP2007-93598A

SUMMARY OF INVENTION

Technical Problem

Therefore, the present invention has been made to solve the above defect, and an essential object thereof is to provide an optical measurement device capable of preventing a relative displacement from occurring between a projection optical system member and a light-receiving optical member so as to be able to ensure measurement accuracy even in the case where a material having a large rate of change in shape with respect to a temperature change is necessarily used as a cell material in such a case of measuring, e.g., a degree of contamination of a chemical solution for use in a semiconductor process.

Solution to Problem

Accordingly, an optical measurement device according to the present invention is adapted to measure characteristics of a measurement targeted fluid based on an inspection light transmitted through the measurement targeted fluid. The optical measurement device includes a cell having an internal space for accommodating or allowing the measurement targeted fluid to flow therein and provided with a pair of through holes opposing each other for transmitting the inspection light through the internal space, wherein each of the through holes is air-tightly or fluid-tightly sealed with a transparent member; a projection optical system member having a light projection port for projecting the inspection light; a light-receiving optical system member having a light introduction port for receiving the inspection light transmitted through the internal space; and a base member for supporting the cell, the projection optical system member, and the light-receiving optical system member in common, in a configuration in which respective gaps are formed between the cell and each of the projection optical system member and the light-receiving optical system member, so as to accommodate a relative movement therebetween in a predetermined range along a direction perpendicular to an optical axis of the inspection light.

With this arrangement, since the cell and the respective optical system members are supported by the base member and the gaps are formed between the cell and the respective optical system members so as to accommodate a relative movement therebetween in a predetermined range along a direction perpendicular to the optical axis direction of the inspection light, even if the cell is deformed by a temperature change, the displacement of the optical axis can be reduced as much as possible without occurrence of a substantial displacement in each of the optical system members, and therefore the measurement accuracy can be ensured.

In order to reduce thermal deformations of the respective optical system members and the base member, it is desirable that the respective optical system members and the base member mainly include materials each having a smaller rate of change in shape with respect to a temperature change than that of a main constituent material of the cell.

In order to minimize a deformation effect of the cell with respect to the base member, the base member is preferably connected to only one surface of the cell.

With a space formed by interposing a spacer between the cell and the base member, transfer of heat of the measurement targeted fluid flowing through the cell to the base member can be suppressed so as to reduce a thermal deformation of the base member, and thus a relative displacement between the projection optical system member and the light-receiving optical system member can be more effectively prevented.

In order to minimize a distance between the respective optical system members as small as possible for compacting a size while preventing a stray light, it is desirable that the respective transparent member sealing each of the through holes is disposed within each of the through holes, and the projection optical system member is provided with a protrusion formed with the light projection port at a tip thereof and the light-receiving optical system member is provided with a protrusion formed with the light introduction port at a tip thereof, so that each protrusion is fitted to an outer surface side with respect to the transparent member in each of the through holes so as to form gaps between an inner peripheral surface of each of the through holes and an outer peripheral surface of each protrusion.

With an elastic ring interposed between the inner peripheral surface of the through hole and the outer peripheral surface of the protrusion, the transparent member can be prevented from being contaminated by substances existing in a peripheral atmosphere such as leakage substances passed through a wall of a pipe.

The cell may be provided with a cell body including the internal space; a pair of pressing members mainly including a member having a smaller rate of change in shape with respect to a temperature change than that of the cell body and attached to respective surfaces of the cell perpendicular to the optical axis; and a connecting member mainly including a member having a smaller rate of change in shape with respect to a temperature change than that of the cell body and connecting the pair of pressing members so as not to substantially change a spaced distance between the respective pressing members. With this arrangement, it can be prevented that the distance between the transparent members is changed by a deformation of the cell body to affect the measurement accuracy.

Advantageous Effects of Invention

Therefore, according to the present invention, even in the case where a material having a large rate of change in shape with respect to a temperature change is necessarily used as a cell material in such a case of measuring, e.g., a degree of contamination of a chemical solution for use in a semiconductor process, it becomes possible to prevent a relative displacement from occurring between the projection optical system member and the light-receiving optical member so as to be able to ensure the measurement accuracy.

DESCRIPTION OF EMBODIMENTS

The following describes an optical measurement device 100 according to an embodiment of the present invention with reference to the accompanying drawings.
(First Embodiment)

Figure 1:
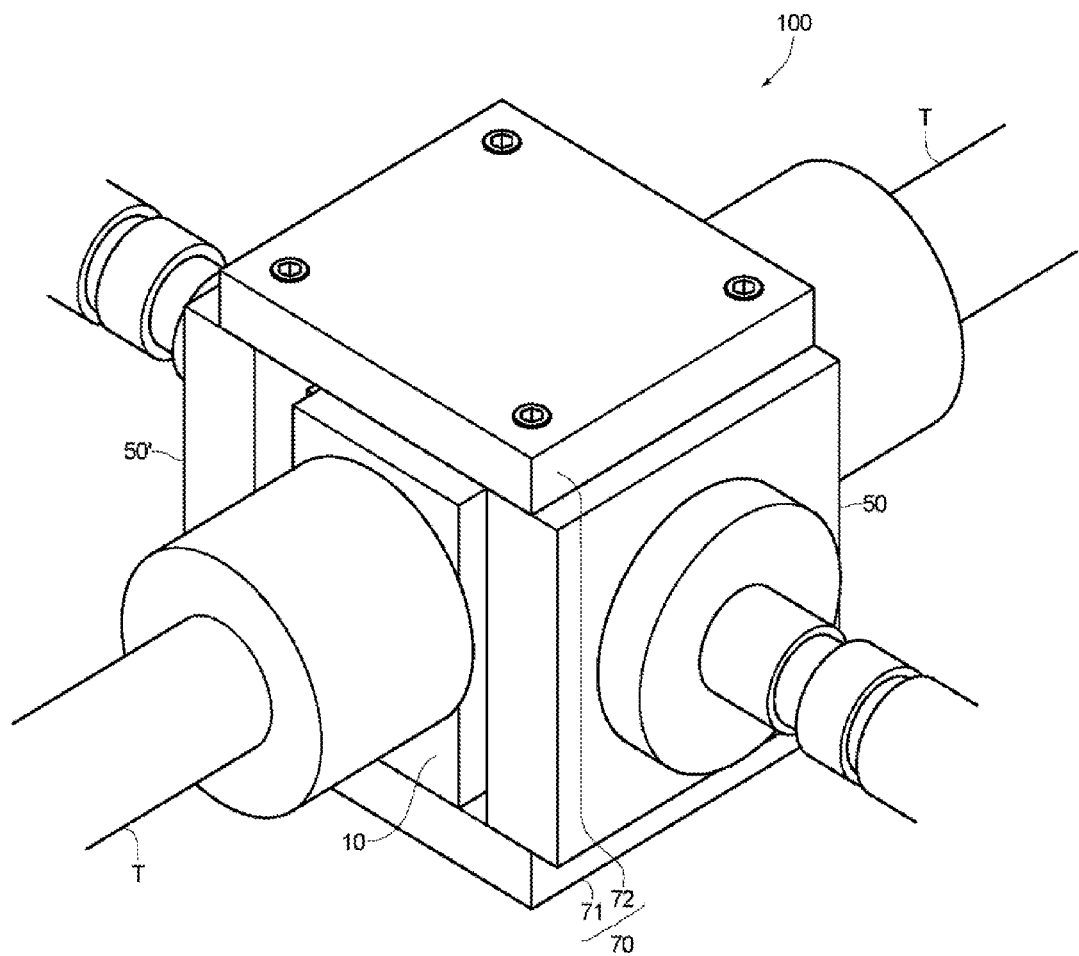
FIG. 1 is a perspective view of an optical measurement device according to a first embodiment of the present invention.

The optical measurement device 100 according to the first embodiment is adapted to irradiate a measurement targeted fluid of a chemical solution for cleaning a semiconductor wafer with an inspection light so as to measure a degree of contamination of the measurement targeted fluid based on the inspection light transmitted through the measurement targeted fluid. Specifically, as shown in FIG. 1, the optical measurement device 100 includes a flow-type cell 10 in which the measurement targeted fluid flows, a projection optical system member 50 for projecting the inspection light to the measurement targeted fluid flowing in the cell 10, a light-receiving optical system member 50' for receiving the inspection light transmitted through the measurement targeted fluid flowing in the cell 10, and a supporting frame body 70 for securely supporting the cell 10 and each of the optical system members 50 and 50'.

Figure 2:
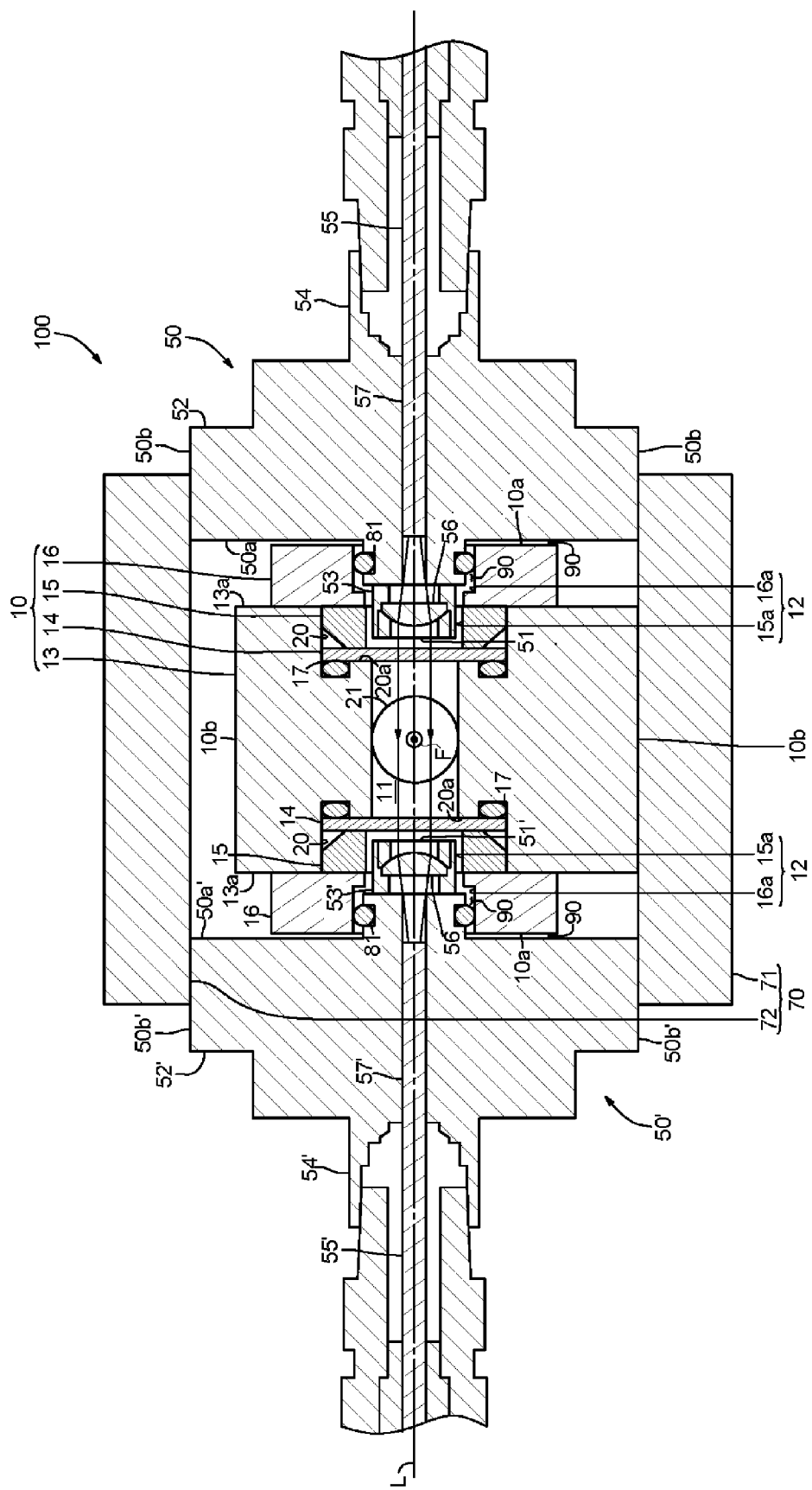
FIG. 2 is a longitudinal section view of the optical measurement device according to the same embodiment.
Figure 3:
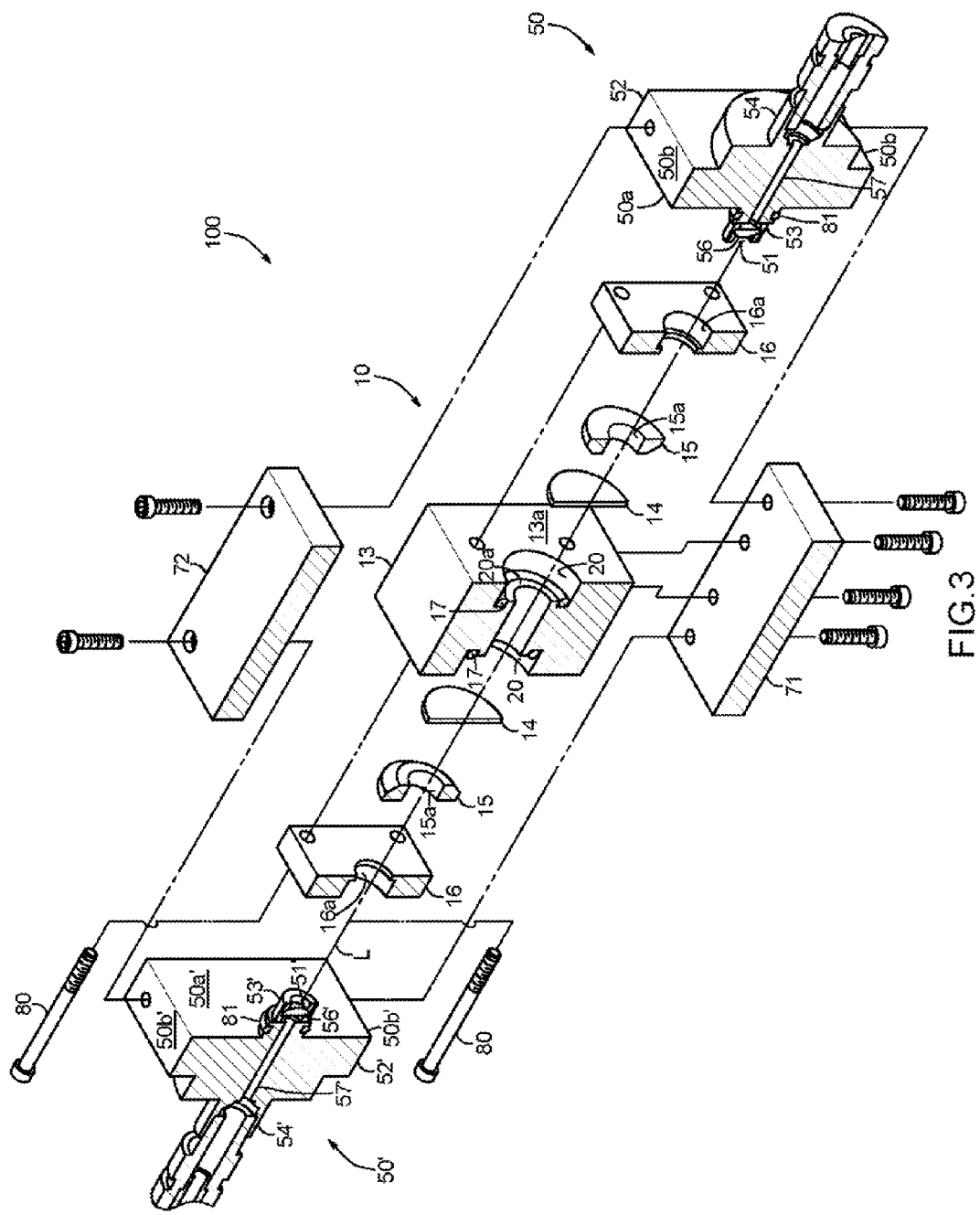
FIG. 3 is an exploded perspective view of the optical measurement device according to the same embodiment.

Various parts of the optical measurement device 100 are described below. As shown in FIGS. 2 and 3, the cell 10 is schematically formed of a hollow block shaped body having a cell body 13 as a major constituent member thereof. The cell body 13 is schematically formed of a hollow rectangular shape with its one pair of opposing sidewalls provided with an inlet port 21 and an outlet port respectively opened to be communicated with an internal space 11 thereof. As shown in FIG. 1, pipes T for inflow and outflow of the measurement targeted fluid are respectively connected to the inlet port 21 and the outlet port so that the measurement targeted fluid is introduced into the internal space 11 of the cell body 13 from the inlet port 21 and is derived from the outlet port. Meanwhile, inspection light transmission holes 20 for transmitting the inspection light are respectively opened in another pair of opposing sidewalls 13a (referred to as "transmission hole forming sides 13a" hereinafter) of the cell body 13. The inspection light is introduced into the internal space 11 of the cell body 13 through one of the inspection light transmission holes 20 and is derived from the other of the inspection light transmission holes 20.

The cell 10 is further provided with a pair of schematically disc-shaped transparent plates 14 (each corresponding to a transparent member in claims) for closing the inspection light transmission holes 20. More specifically, a step portion 20a is formed inside each of the inspection light transmission holes 20 and the transparent plate 14 is pressed in close contact with the step portion 20a through an O ring 17. Furthermore, in order to press the transparent plate 14, a pressing member 16 and a spacer ring 15 are provided. The pressing member 16 has a schematically rectangular plate shape which is larger in size than the inspection light transmission hole 20 and has a first hole 16a penetrating therethrough in a direction of an optical axis L. The pressing member 16 is attached to the transmission hole forming side 13a of the cell body 13 so as to press the transparent plate 14 by way of the spacer ring 15 accommodated in the inspection light transmission hole 20 while pressing the transmission hole forming side 13a of the cell body 13. In addition, a pair of the pressing members 16 is coupled to each other by connecting members 80 such as bolts so that the distance therebetween is substantially unchanged.

In the cell 10 configured like this, a pair of opposing through holes 12 are formed. More specifically, the pair of through holes 12 are communicated with the internal space 11 and are respectively opened to a pair of opposing surfaces 10a (also, each referred to as "through hole forming surface 10a" hereinafter) perpendicular to the optical axis direction L of the inspection light in the cell 10. Each of the through holes 12 is formed of the first hole 16a of the pressing member 16 and a second hole 15a having a diameter corresponding to an inner diameter of the spacer ring 15, and each of the through holes 12 has a bowl-like shape as it becomes narrower in a stepwise manner toward a side of the internal space 11.

Referring to each of the members composing the cell 10 in terms of materials, the cell body 13 and the spacer ring 15 are formed with use of a corrosion resistant PTFE (Teflon) resin. In contrast, as to the pressing member 16 and the connecting member of bolt 80, a material having a smaller rate of change with respect to a temperature change than that of the cell body 13 is used. Herein, a poly-phenylene-sulfide resin (also, referred to as "PPS resin" hereinafter) is used as a material of the pressing member 16 and a stainless steel is used as a material of the bolt 80. In addition, the transparent plate 14 is made of sapphire.

The projection optical system member 50 is installed in a manner of facing one of the through hole forming surfaces 10*a* of the cell 10 so as to project the inspection light into the internal space 11 of the cell 10. As shown in FIGS. 2 and 3, the projection optical system member 50 includes a schematically rectangular plate shaped main body block 52, a schematically cylindrical shaped protrusion 53 provided on a surface (also, referred to as "protrusion forming surface 50*a*" hereinafter) of the main body block 52 opposing the cell 10 and having a light projection port 51 formed at its tip end, an attachment port 54 provided on a back surface of the protrusion forming surface 50*a* for attaching an optical fiber 55 as light transfer means. An optical fiber holding hole 57 is formed to extend from the attachment port 54 to the light projection port 51 while penetrating the main body block 52 in the optical axis direction L. The optical fiber 55 connected to a light source (not shown) is inserted through the optical fiber holding hole 57. In order to collimate the lights projected from the optical fiber 55, a plano-convex lens 56 is attached inside the protrusion 53 with its convex side directed to the internal space 11 of the cell 10. The main body block 52, protrusion 53 and attachment port 54 are formed with use of a PPS resin material which has a smaller rate of change in shape with respect to a temperature change than that of the cell body 13.

The light-receiving optical system member 50' is installed in a manner of facing the other surface of the through hole forming surfaces 10*a* of the cell 10 so as to receive the inspection light transmitted through the internal space 11 of the cell 10 through a light introduction port 51'. As shown in FIG. 2, since the light-receiving optical system member 50' is symmetrical in shape to the projection optical system member 50, a detailed description thereof is omitted here. Each symbol of the parts of the light-receiving optical system member 50' is represented by a dashed symbol of each of the corresponding parts of the projection optical system member 50.

The supporting frame body 70 includes a base member 71 and a top plate member 72. The base member 71 has a schematically rectangular plate shape to commonly support the cell 10 and each of the optical system members 50 and 50'. More specifically, the base member 71 is connected by, e.g., bolts to only one of a pair of opposing surfaces (also, referred to as "frame body attachment surfaces 10*b*, 50*b* and 50*b*'" hereinafter) which are parallel to both the optical axis direction L of the inspection light and a flowing direction F of the measurement targeted fluid in the cell 10 and the respective optical system members 50 and 50'. The top plate member 72 has a schematically rectangular shape to be connected by, e.g., bolts to the other surface of the frame body attachment surfaces 50*b* and 50*b*' of the respective optical system members 50 and 50'. The base member 71 and the top plate member 72 are formed with use of a PPS resin material having a smaller rate of change in shape to a temperature change than that of the cell body 13.

In the present embodiment, in a state that the cell 10 and the respective optical system members 50 and 50' are supported by the supporting frame body 70, a pair of gaps 90 are formed for accommodating a relative movement between the cell 10 and the respective optical system members 50 and 50' in a direction perpendicular to the optical axis direction L of the inspection light. Thus, each of the protrusions 53 and 53' of the optical system members 50 and 50' is fitted at an outer surface side than the location of the transparent plate 14 in the through hole 12 of the cell 10. More specifically, as to a forming position of each of the gaps 90, each of the gaps 90 is formed between inner peripheral surfaces of the through holes 12 of the cell 10 and an outer peripheral surface of each of the protrusions 53 and 53' of the respective optical system members 50 and 50'. As to a size of the gap 90, for example, in the case where the measurement targeted fluid is measured within a specified temperature range of the optical measurement device 100, the size is set to be large enough in a degree that the cell 10 and each of the optical system members 50 and 50' are not directly contacted even if the cell 10 is deformed due to an effect of a temperature change to cause a relative movement between the cell 10 and each of the optical system members 50 and 50'.

Further, in the present embodiment, the pair of gaps 90 are formed to accommodate a relative movement along the optical axis direction L of the inspection light between the cell 10 and the respective optical system members 50 and 50' so as to prevent the cell 10 and the respective optical system members 50 and 50' from being brought into direct contact. Each of the gaps 90 is formed between each of the through hole forming surface 10*a* of the cell 10 and each of the protrusion forming surfaces 50*a* and 50*a*' of the respective optical system members 50 and 50'. In this configuration, the cell 10 and the top plate member 72 are separated from each other. That is, a distance between the frame body attachment surfaces 10*b* of the cell 10 is set to be smaller than a distance between the frame body attachment surfaces 50*b* and 50*b*' of the respective optical system members 50 and 50'.

In addition, each of the protrusions 53 and 53' has a tapered shape as it becomes narrower in a stepwise manner toward the tip end thereof. An annular groove for attaching an elastic ring 81 is formed in the outer peripheral surface of each of the protrusions 53 and 53'. As shown in FIG. 2, the elastic ring 81 is interposed between the inner peripheral surface of the through hole 12 of the cell 10 and an outer peripheral surface of each of the protrusions 53 and 53' so as to constitute an air-tight or fluid-tight sealing between the cell 10 and each of the protrusions 53 and 53'.

According to the present embodiment, since the cell 10 and the respective optical system members 50 and 50' are supported by the base member 71 and the gaps 90 are formed between the cell 10 and the respective optical system members 50 and 50' so as to accommodate a relative movement therebetween in a predetermined range along a direction perpendicular to the optical axis direction L of the inspection light, even if the cell 10 is deformed by a temperature change, the displacement of the optical axis can be reduced as much as possible without occurrence of a substantial displacement in each of the optical system members 50 and 50', and therefore the measurement accuracy can be ensured.

Moreover, the gap 90 is formed in the optical axis direction L between the cell 10 and each of the optical system members 50 and 50', an effect of a temperature change of the cell 10 can be less affected, and a displacement in optical axis of each of the optical system members 50 and 50' can be further reduced. Furthermore, since each of the through holes 12 of the cell 10 and each of the protrusions 53 and 53' of the respective optical system members 50 and 50' are formed to have tapered shapes to be narrower in a stepwise manner as they move closer to the internal space 11 of the cell 10, entrance of a stray light can be effectively prevented. The shape of the through hole 12 can be changed in accordance with a temperature, etc., of the measurement targeted fluid by replacing the pressing member 16 and the spacer ring 15. In addition, since the members composing the cell body 13 and the spacer ring 15 have the same rate of change in shape with respect to a temperature change, even if the cell body 13 is affected by heat and the inspection light transmission hole 20 for accommodating the spacer ring 15 is deformed, the spacer ring 15 is similarly subject to thermal deformation, and therefore the spacer ring 15 can keep a state of transferring a pressing force from the pressing member 16 to the transparent plate 14 so that the through hole 12 can be kept in a state of being air-tightly and fluid-tightly sealed.

(Second Embodiment)

Figure 4:
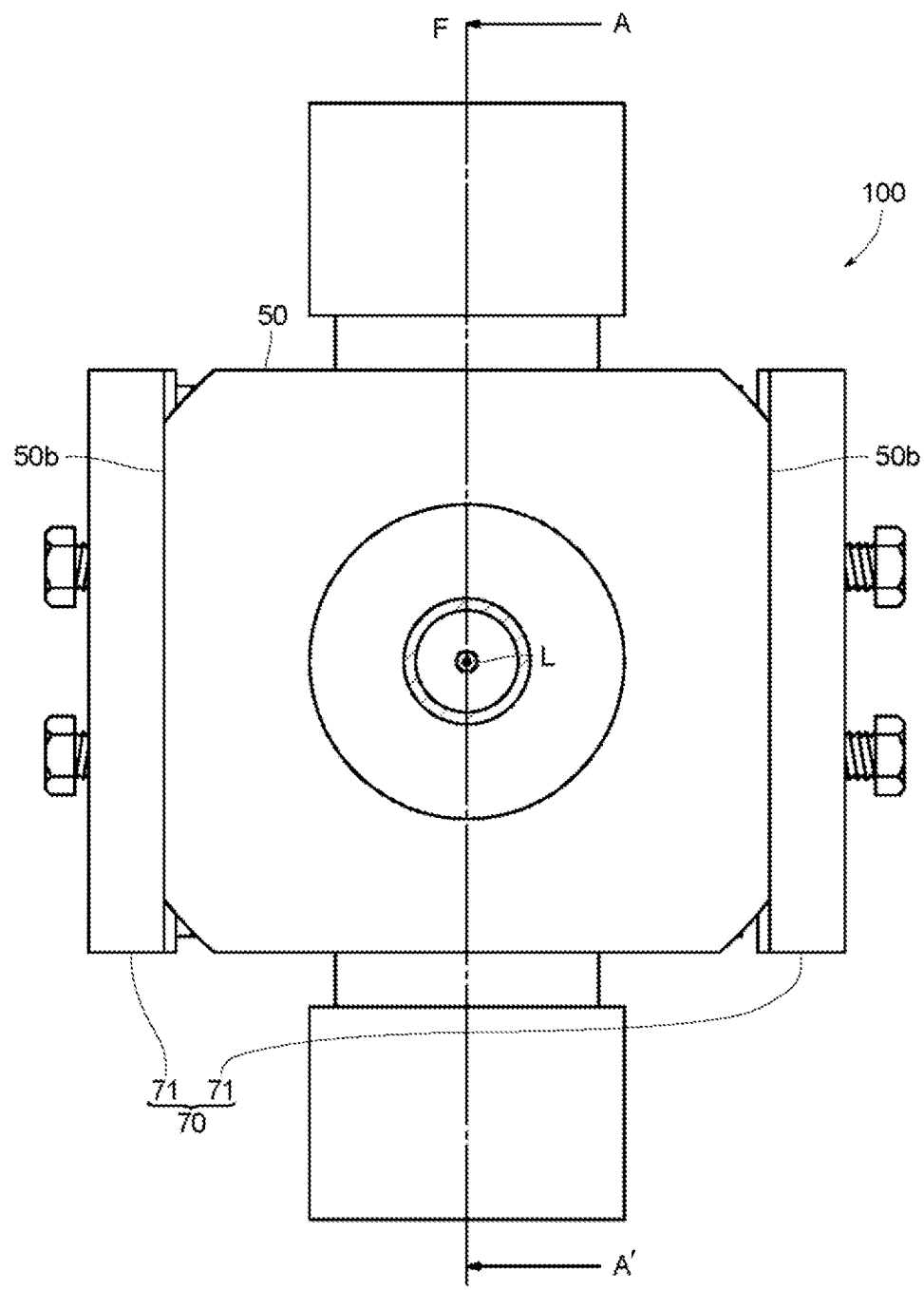
FIG. 4 is a side view of an optical measurement device according to a second embodiment of the present invention.
Figure 5:
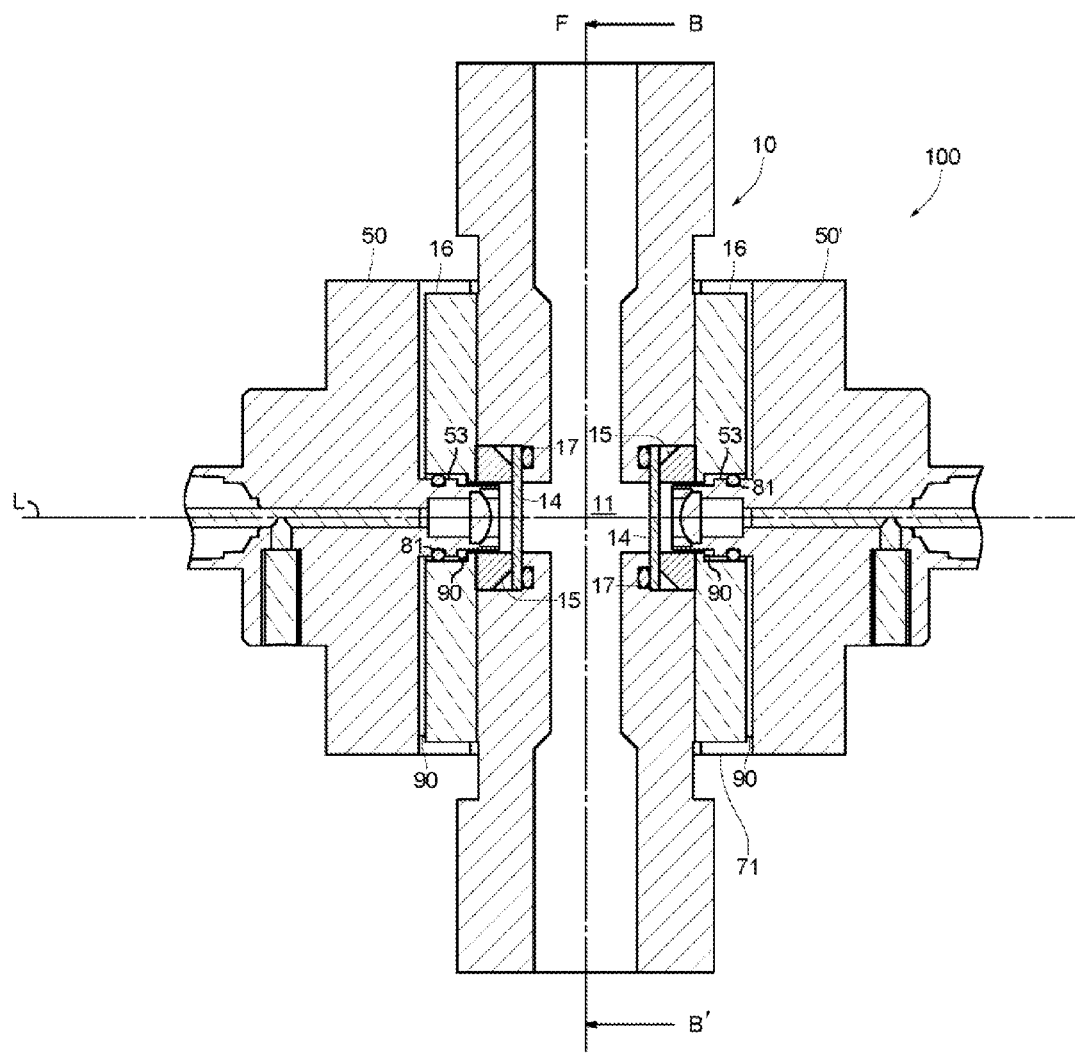
FIG. 5 is a sectional view across a line A-A' of the optical measurement device according to the same embodiment as in FIG. 4.
Figure 6:
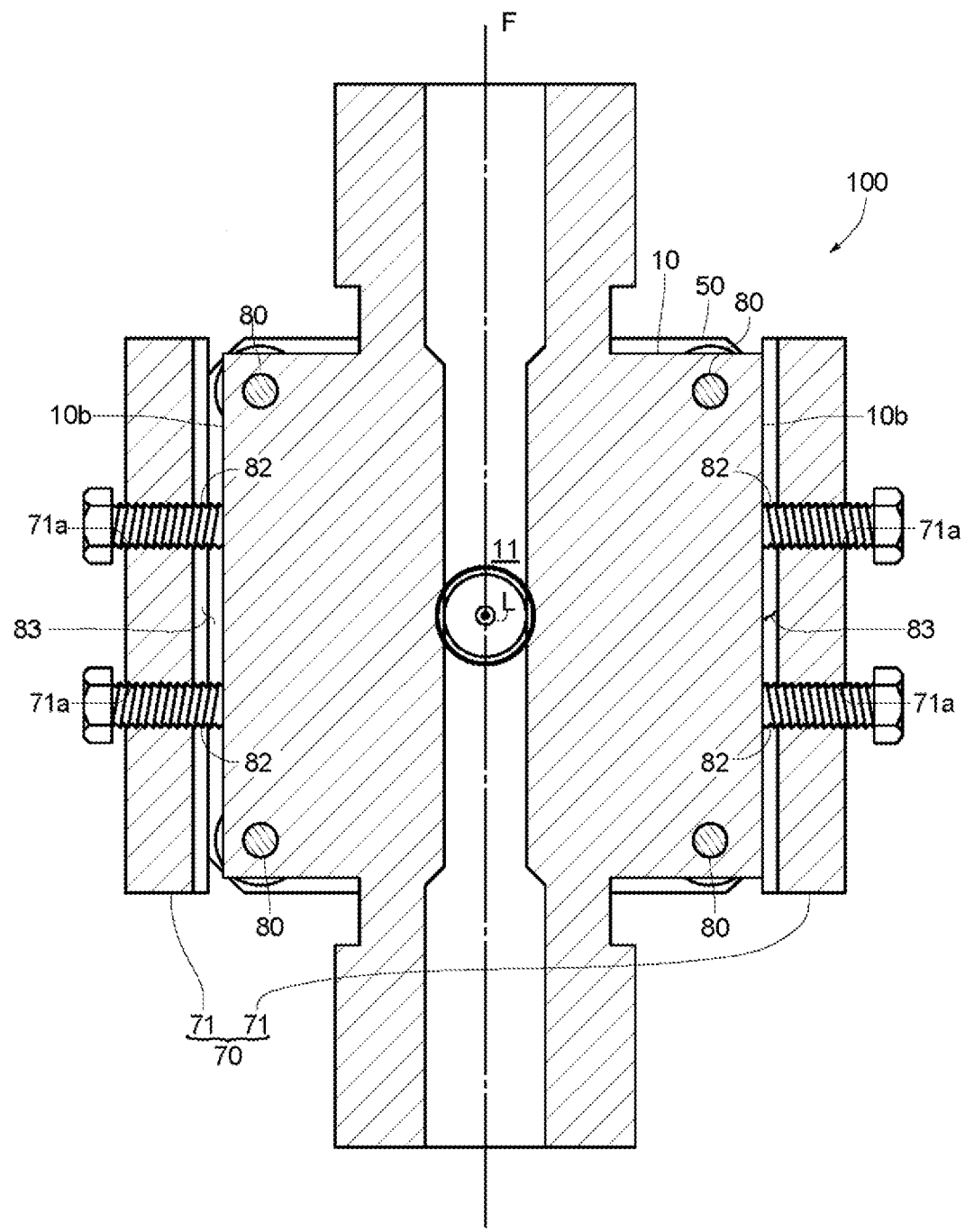
FIG. 6 is a sectional view across a line B-B' of the optical measurement device according to the same embodiment as in FIG. 5.

Next, the optical measurement device according to a second embodiment of the present invention is described with reference to FIGS. 4 to 6. The supporting frame body 70 includes a pair of base members 71 each having a schematically rectangular shape. Each base member 71 is disposed in a manner of facing the frame body attachment surfaces 10b, 50b and 50b' of the cell 10 and the respective optical system members 50 and 50'. As shown in FIG. 4, the pair of base members 71 are fixed to the respective optical system members 50 and 50' by, e.g., bolts (not shown) so as not to move with respect to the respective optical system members 50 and 50' without changing a distance between the pair of the base members 71. In contrast, as shown in FIG. 6, each of the base members 71 is attached to the cell 10 with spacers 82 interposed and spaces 83 formed therebetween. More specifically, each of the spacers 82 is a protrusion protruding from one surface of the base member 71 and it is implemented here by a tip end of a bolt that is screwed with a female hole 71a and penetrates the base member 71. Thus, the tip ends of the bolts press the pair of frame body attachment surfaces 10b so that the cell 10 is securely supported by the pair of base members in a sandwiched manner. Since the other configurations are similar to the first embodiment described above, the explanation thereof is omitted with use of the same reference numerals.

According to the present embodiment, since the spacers 82 are interposed with the spaces 83 formed between the cell 10 and the respective base members 71, the transfer of the heat of the measurement targeted fluid flowing in the cell 10 can be suppressed and the thermal deformation of the base members 71 can be reduced. As a result, a relative displacement between the projection optical system member 50 and the light-receiving optical system member 50' supported by the base members 71 can be more effectively prevented.

(Third Embodiment)

Figure 7:
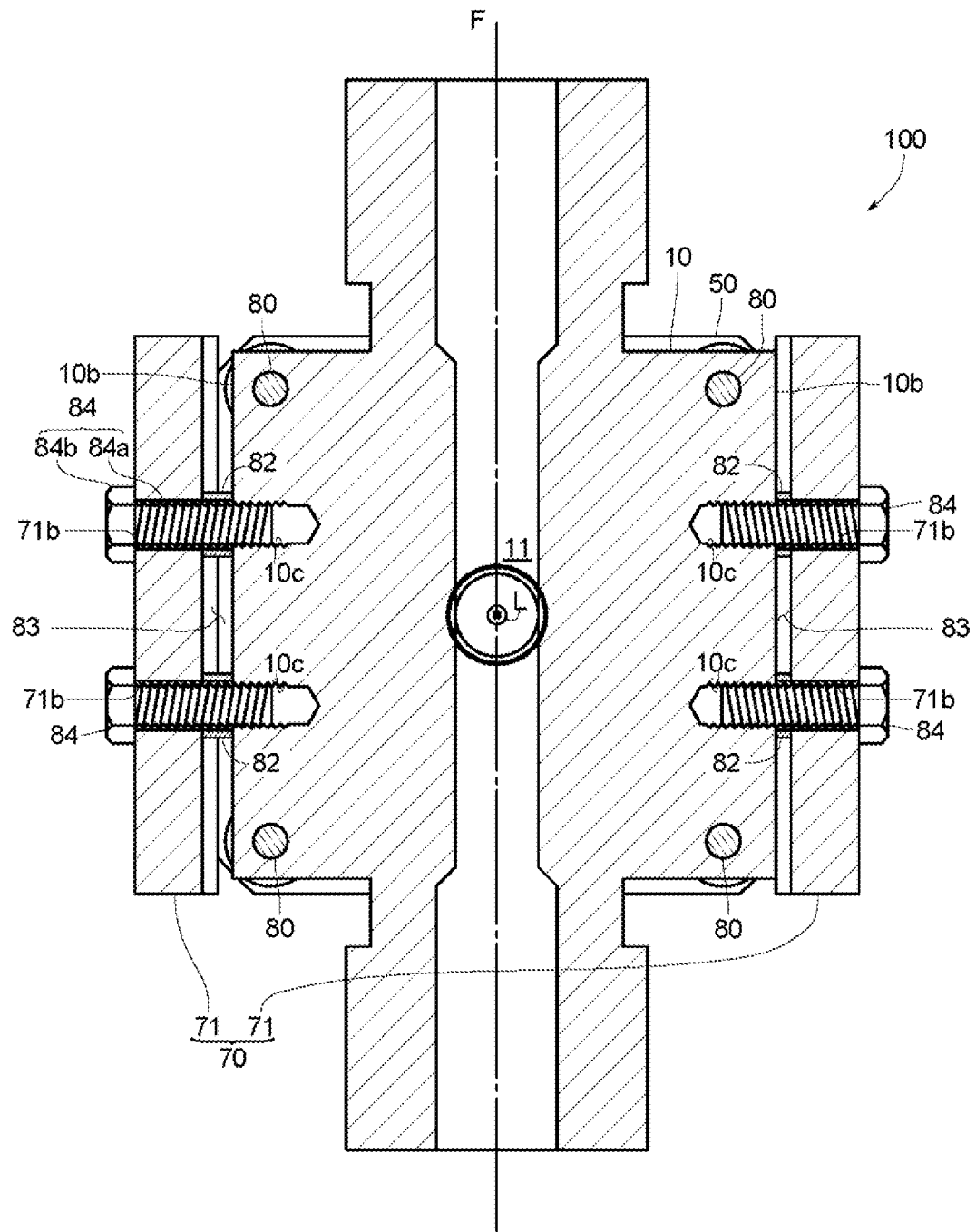
FIG. 7 is a lateral section view of an optical measurement device according to a third embodiment of the present invention.

The optical measurement device 100 according to the third embodiment of the present invention is further described with reference to FIG. 7. In the third embodiment, although a space 83 is formed between the cell 10 and the base member 71 similarly to the second embodiment, these parts are connected in another manner different from the aspect in the second embodiment. Specifically, the cell 10 and the base member 71 are connected by connecting members 84 (bolts are used in this example) each of which penetrates an insertion hole 71b which is not a female screw hole of the base member 71. The connecting member 84 includes a shank 84a which is firmly screwed into a female screw hole 10c formed in the cell 10 and a head portion 84b pressing the base member 71 toward the frame body attachment surface 10b formed in the cell 10. The shank 84a also penetrates a schematically ring shaped spacer 82 interposed between the cell 10 and the base member 71. In this state, the space 83 is formed between the cell 10 and the base member 71. Since the other configurations are similar to the second embodiment described above, the explanation thereof is omitted with use of the same reference numerals.

According to the present embodiment, since the base member 71 and the cell 10 are connected by the connecting members 84, a pair of base members 71 may be used, and also the cell 10 and the respective optical system members 50 and 50' may be commonly supported by a single base member 71.

(Fourth Embodiment)

Figure 8:
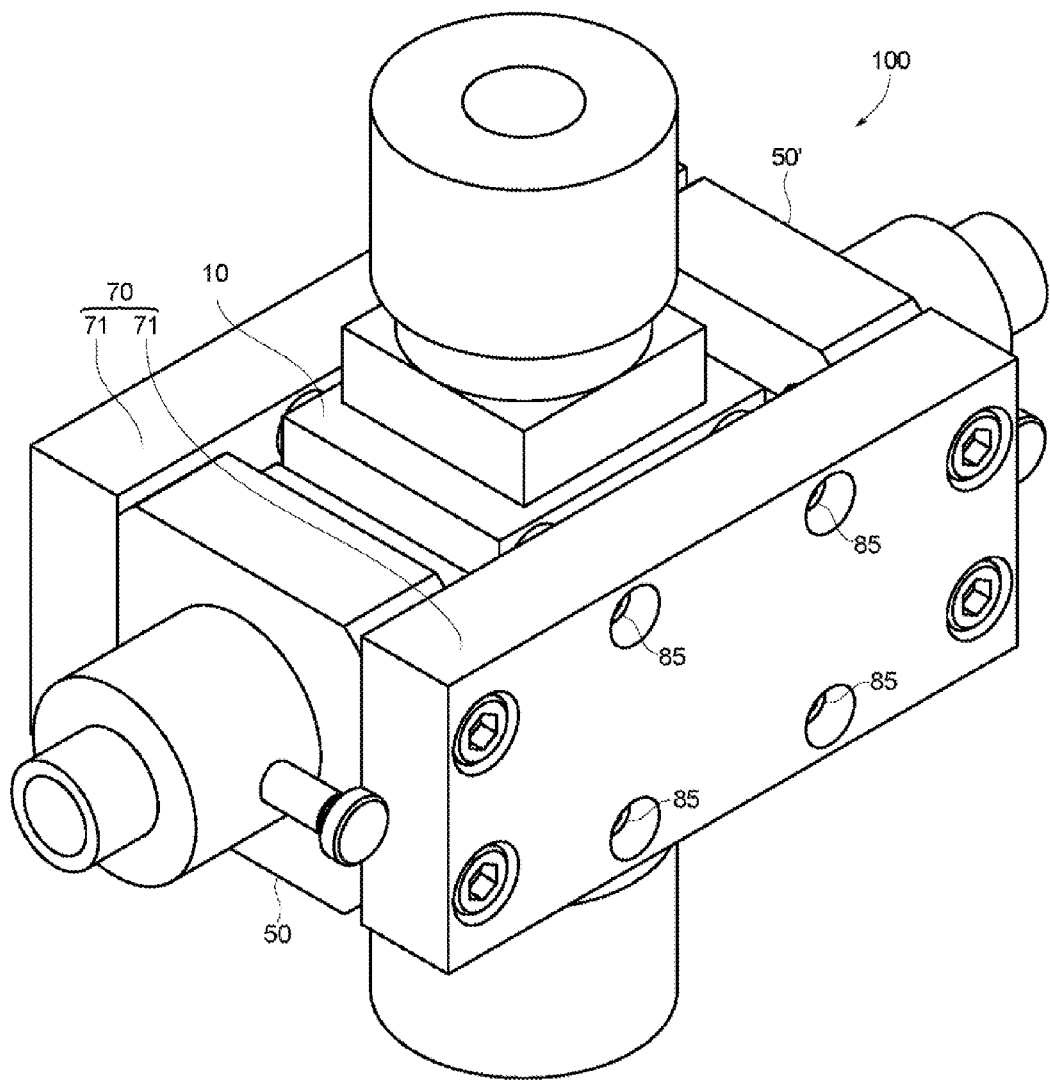
FIG. 8 is a perspective view of an optical measurement device according to a fourth embodiment of the present invention.
Figure 9:
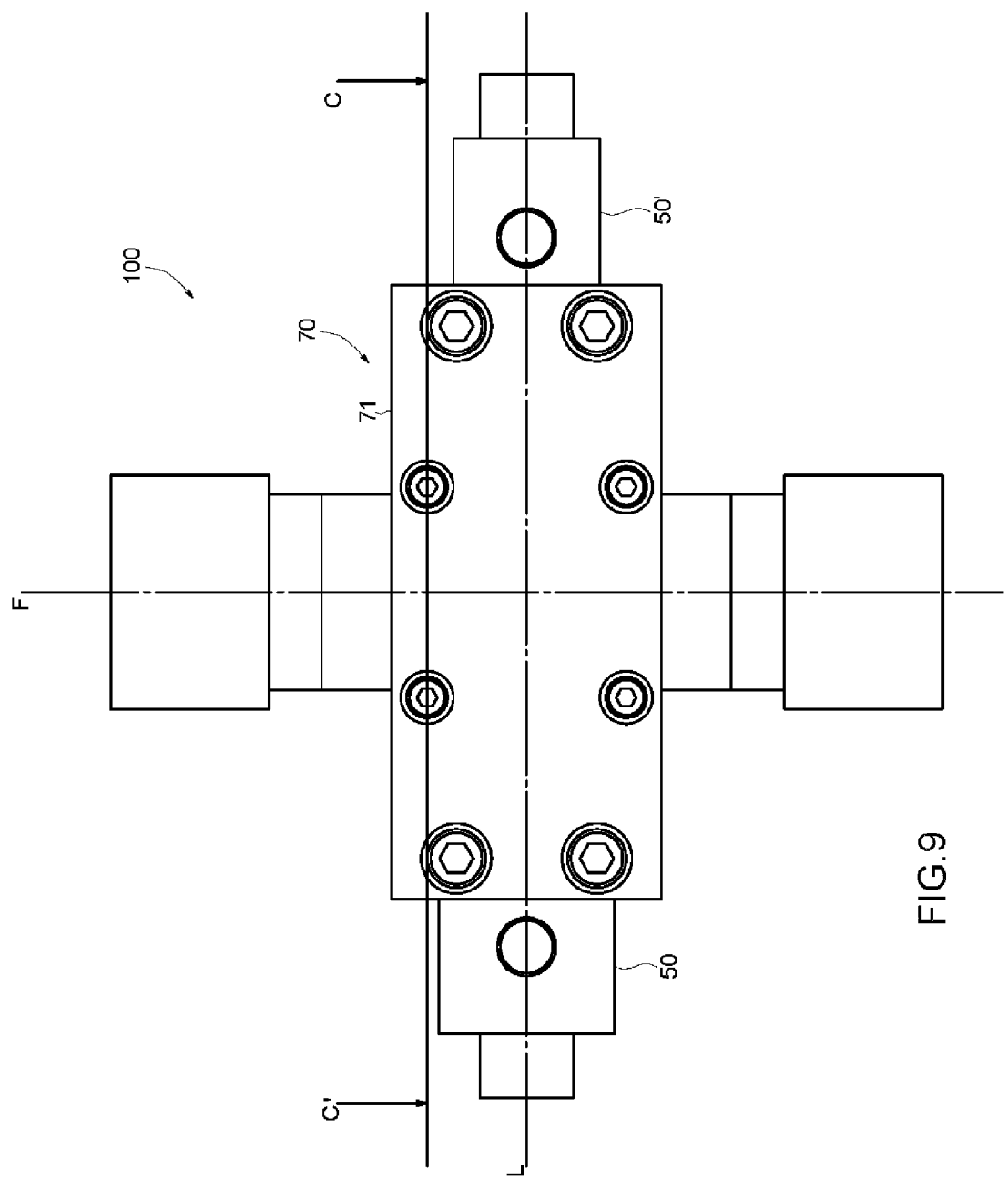
FIG. 9 is a side view of the optical measurement device according to the same embodiment as FIG. 8.
Figure 10:
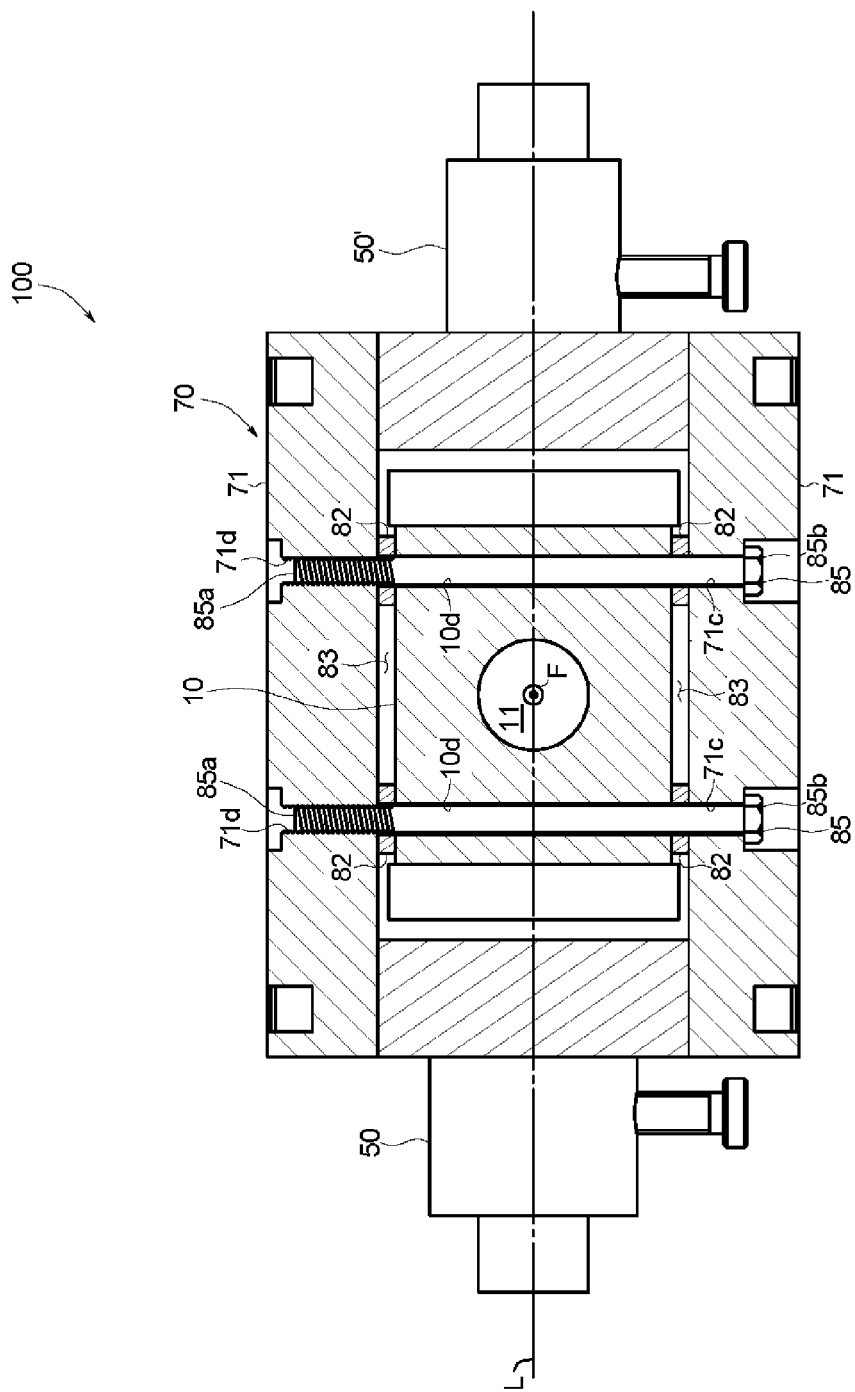
FIG. 10 is a sectional view across a line C-C' of the optical measurement device according to the same embodiment as in FIG. 9.

The optical measurement device 100 according to a fourth embodiment of the present invention is described with reference to FIGS. 8 to 10. The fourth embodiment is different from the other embodiments in terms of attaching the cell 10 and the base member 71. As shown in FIG. 8, the cell 10 is sandwiched between a pair of base members 71 and the pair of base members 71 are connected to each other by connecting members 85 (bolts in this example). As shown in FIG. 10, a shank 85a of each of the connecting members 85 penetrates an insertion hole 71c formed in one of the base members 71 and an insertion hole 10d formed in the cell 10 wherein these insertion holes 71c and 10d are not female screw holes and the shank 85a is screwed into a female screw hole 71d formed in the other of the base members 71. A head portion 85b of each connecting member 85 presses one of the base members 71 toward the other of the base members 71. Thus, the cell 10 is tightly sandwiched by pressing between the pair of base members 71.

Further, the shank 85a of the connecting member penetrates a schematically ring-shaped spacer 82 interposed between the cell 10 and each of the base members 71. Thus, a space 83 is formed between the cell 10 and each of the base members 71. Since the other configurations are similar to the second embodiment described above, the explanation thereof is omitted with use of the same reference numerals.

It is noted that the present invention is not limited to these embodiments. For example, in the present embodiment, although a flow-type cell is used for the measurement targeted fluid to flow through the internal space thereof, a batch-type cell may be used for the measurement targeted fluid to be accommodated in the internal space thereof for use in measurement in a batch process.

In addition, each optical system member is adapted to interpose an optical fiber as light transfer means between a light source and a light projection port or between a light receiving element and a light introduction port, the light source or the light receiving element may be directly attached to each optical system member without interposing the light transfer means.

It is only necessary that each optical system member mainly includes a member having a smaller rate of change in shape with respect to a temperature change than that of a cell body, and it is sufficient that each main body block includes such a member.

Although the spacer is, e.g., a protrusion protruding from a base member or a member separately provided from the base member and the cell, the spacer may be a protrusion protruding from the cell and also may be an appropriate combination thereof. Although a bolt is used as the connecting member, a schematically bolt-like shaped member having a shank and head portion may be used as the connecting member.

Although the through hole of the cell and the protrusion of each optical system member are formed to be continuously narrower as they close toward the internal space of the cell and have stepwise shapes formed with one or more steps, they may be gradually expanded wider as they close toward the internal space of the cell. It may be also possible that any one of the through hole and the protrusion is stepwise shaped and the other is tapered. There may be provided a light shield portion interposed between the through hole and the protrusion or protruding from at least any one thereof without a stepwise shape. In short, it may be sufficient that the gap formed between the through hole and the protrusion is formed to be bent so as not to linearly penetrate the external space and the internal space of the cell or the light shield portion is provided to block an optical path of the light transmitting through the gap formed between the through hole and the protrusion. In addition, the present invention may be variously changed or modified within a range unless it departs from the spirit of the present invention.

It should be understood that the embodiments herein are illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

Explanation Of Reference Characters

100 . . . Optical measurement device
10 . . . Cell
11 . . . Internal space
12 . . . Through hole
13 . . . Cell body
14 . . . Transparent plate
50 . . . Projection optical system member
51 . . . Light projection port
50' . . . Light-receiving optical system member
51' . . . Light introduction port
71 . . . Base member
80 . . . Connecting member
81 . . . Elastic ring
90 . . . Gap
L . . . Optical axis
F . . . Flow direction of measurement targeted fluid

The invention claimed is:

1. An optical measurement device adapted to measure characteristics of a measurement targeted fluid based on an inspection light transmitted through the measurement targeted fluid, comprising:
 a cell having an internal space for accommodating or allowing the measurement targeted fluid to flow therein and provided with a pair of through holes opposing each other for transmitting the inspection light through the internal space, wherein each of the through holes is air-tightly or fluid-tightly sealed with a transparent member;
 a projection optical system member having a light projection port for projecting the inspection light;
 a light-receiving optical system member having a light introduction port for receiving the inspection light transmitted through the internal space;
 a base member for supporting the cell, the projection optical system member, and the light-receiving optical system member in common; and
 gaps between through hole forming surfaces of the cell and surfaces of respective optical system members arranged facing the through hole forming surfaces are formed along a line in a direction perpendicular to an optical axis of the inspection light.

2. The optical measurement device according to claim 1, wherein each respective optical system member and the base member mainly include materials each having a smaller rate of change in shape with respect to a temperature change than that of the cell.

3. The optical measurement device according to claim 1, wherein the base member is connected to only one surface of the cell.

4. The optical measurement device according to claim 1, wherein a spacer is interposed between the cell and the base member so as to form a space.

5. The optical measurement device according to claim 1, wherein the respective transparent member sealing each of the through holes is disposed within each of the through holes, wherein
 the projection optical system member is provided with a protrusion formed with the light projection port at a tip thereof and the light-receiving optical system member is provided with a protrusion formed with the light introduction port at a tip thereof, and wherein
 each protrusion is fitted to an outer surface side with respect to the transparent member in each of the through holes so as to form the gaps between an inner peripheral surface of each of the through holes and an outer peripheral surface of each protrusion.

6. The optical measurement device according to claim 5, wherein an elastic ring is interposed between the inner peripheral surface of each of the through holes and the outer peripheral surface of each protrusion.

7. The optical measurement device according to claim 1, wherein the cell comprises:
 a cell body including the internal space;
 a pair of pressing members mainly including a member having a smaller rate of change in shape with respect to a temperature change than that of the cell body and attached to respective surfaces of the cell perpendicular to the optical axis; and
 a connecting member having a smaller rate of change in shape with respect to a temperature change than that of the cell body and connecting the pair of pressing members so as not to substantially change a spaced distance between each respective pressing member.

* * * * *